March 31, 1959 E. S. BOERNER Plant Pat. 1,824
CHRYSANTHEMUM PLANT
Filed Aug. 21, 1958
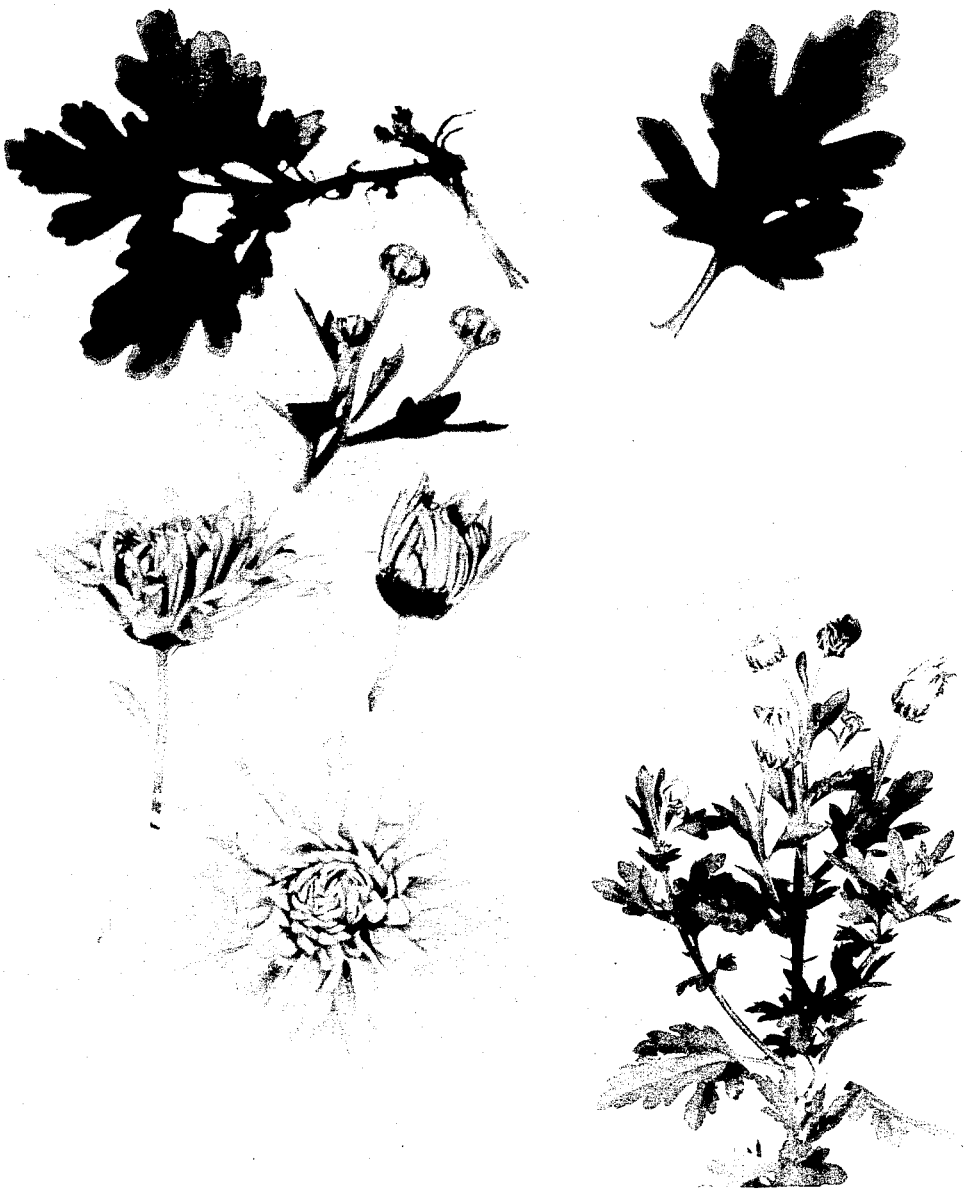
Inventor.
E. S. Boerner
By: Robb & Robb
Attorneys.

United States Patent Office

Plant Pat. 1,824
Patented Mar. 31, 1959

1,824

CHRYSANTHEMUM PLANT

Eugene S. Boerner, Newark, N.Y., assignor to Jackson & Perkins Company, Newark, N.Y., a corporation of New York Application August 21, 1958, Serial No. 756,495

1 Claim. (Cl. 47—60)

The present invention relates to a new and distinct variety of chrysanthemum plant of the decorative type, which was originated by me by crossing the variety "W. F. Snyder" (unpatented) with the variety "Kingbird" (Plant Patent No. 1,306).

The primary objective of this breeding was to produce a new chrystanthemum variety in which the vigorous habit of growth and large flower size typical of the parent variety "Kingbird" are combined with a vivid flower color like that of the parent variety "W. F. Snyder." This objective was fully achieved, along with other improvements, as evidenced by the following characteristics, which are outstanding in the new variety and which distinguish it from its parents as well as from all other varieties of which I am aware:

(1) Vigorous and hardy habits of growth;
(2) Production of many suckers;
(3) Large flower size; and
(4) A distinctive Spinel Pink general color tonality of the flowers.

Asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character, as well as a typical specimen plant which is depicted in black-and-white, as illustrative of the form and habit of growth of the plant.

The following is a detailed description of the new variety, with color terminology in accordance with Ridgway's Color Standards and Nomenclature, as based upon observations made from specimens grown outdoors at Newark, New York, near mid-morning in the latter part of September:

Parentage: "W. F. Snyder" × "Kingbird."

Classification: Decorative.
Growth: Upright; vigorous; attains a height of 2½ feet.
Cold resistance: The plant is very winter hardy in northern New York, burning slightly with late frosts.
Blooming period: In the Newark, New York climatic area, average date of start of bloom is late September, with bloom continuing until frost.

*Flower*

Bud:

*Color.*—When sepals first divide—Light Jasper Red, Plate 13. When petals begin to unfurl—Eugenia Red, Plate 13. When half-blown: inside of petals—Spinel Pink, Plate 26; outside of petals—Vinaceous, Plate 27.
*Peduncle.* — Color — Absinthe Green, Plate 31. Strength—strong.

Bloom:

*Size.*—From 5 inches to 5½ inches.
*Stem.*—Short.
*Form.*—Decorative.
*Petalage.*—Very double.
*Color.*—Center of flower—Spinel Pink, Plate 26. Outer petals—Thulite Pink, Plate 26, lightly overcast with Spinel Pink, Plate 26 on the tip edge of the petal. Base of petals—Citron Green, Plate 31. Inside of petals—Spinel Pink, Plate 26, with lower part of petal lightly overcast with Thulite Pink, Plate 26. Reverse of petals—Venetian Pink, Plate 13.
*Petals.*—Texture—medium. Form—wide; oval.
*Fragrance.*—Characteristic chrysanthemum.

*Plant*

Form: Upright; bushy.
Growth: Free, with many suckers.
Foliage:
*Size.*—Medium.
*Quantity.*—Heavy.
*Color.* — Upper side — Dark Dull Yellow-Green, Plate 32. Under side — Light Elm Green, Plate 17.
*Texture.*—Leathery.

I claim:

A new and distinct variety of chrysanthemum plant of the decorative type, substantially as herein shown and described, characterized particularly as to novelty by the unique combination of vigorous and hardy habits of growth, production of many suckers, large flower size, and a distinctive Spinel Pink general color tonality of the flowers.

No references cited.